(12) United States Patent
Hooper et al.

(10) Patent No.: US 7,071,319 B2
(45) Date of Patent: Jul. 4, 2006

(54) RECOMBINANT ANTIBODIES, AND COMPOSITIONS AND METHODS FOR MAKING AND USING THE SAME

(75) Inventors: Douglas Craig Hooper, Medford, NJ (US); Bernhard Dietzschold, Newton Square, PA (US)

(73) Assignee: Thomas Jefferson University, Philadelphia, PA (US)

( * ) Notice: Subject to any disclaimer, the term of this patent is extended or adjusted under 35 U.S.C. 154(b) by 358 days.

(21) Appl. No.: 10/225,108

(22) Filed: Aug. 21, 2002

(65) Prior Publication Data

US 2003/0157112 A1 Aug. 21, 2003

Related U.S. Application Data

(63) Continuation-in-part of application No. 09/848,832, filed on May 4, 2001.
(60) Provisional application No. 60/314,023, filed on Aug. 21, 2001, and provisional application No. 60/204,518, filed on May 16, 2000.

(51) Int. Cl.
*C07H 21/04* (2006.01)

(52) U.S. Cl. .............................. 536/23.53; 435/320.1; 435/339

(58) Field of Classification Search .............. 424/142.1, 424/147.1, 224.1; 436/93.2, 548; 530/388.15, 530/388.3; 536/23.53
See application file for complete search history.

(56) References Cited

FOREIGN PATENT DOCUMENTS

| EP | 239400 | 3/1987 |
|---|---|---|
| EP | 332424 | 8/1989 |
| EP | 338745 | 1/1995 |
| WO | WO 89/09622 | 10/1989 |
| WO | WO 89/09789 | 10/1989 |
| WO | WO 93/21319 | 10/1993 |

OTHER PUBLICATIONS

Rando, R.F., et al., Curr. Top. Microbiol. Immunol., 187:195–205 (1994).*
Ikematsu, H. et al., J. Immunol., 150:1325–1338 (1993).*
Muller, B.H., J. Virol. Methods, 67:221–233 (1997).*
Cheung, S.C., et al., J. Virol., 66:6714–670 (1992).*
Morimoto et al., "Characterization Of A Unique Variant Of Bat Rabies Virus Responsible For Newly Emerging Human Cases In North America", *Proc. Natl. Acad. Sci. USA*, vol. 93, pp. 5653–5658, (1996).
Dietzschold, B., "Techniques For The Purification Of Rabies Virus, Its Subunits And Recombinants Products," *Laboratory Techniques in Rabies*, Meslin et al., (Eds.) World Health Organization, Geneva, pp. 175–180, (1996).
Plebanski, M. et al., "Primary And Secondary Human In Vitro T–Cell Responses To Soluble Antigens Are Mediated By Subsets Bearing Different CD45 Isoforms", *Immunology*, vol. 75, pp. 86–91, (1992).
Hooper, D., "Rabies Virus", *Manual of Clinical Laboratory Immunology, Part II*, $5^{th}$ ed., N.R. Rose (Ed.), ASM Press, Wash. D.C., pp. 755–760, (1997).
Pearson, W., et al., "Improved Tools For Biological Sequence Comparison", *Proc. Natl. Acad. Sci. USA*, vol. 85, pp. 2444–2448, (1988).
Champion, J.M., et al., "The Development Of Monoclonal Human Rabies Virus–Neutralizing Antibodies As A Substitute For Pooled Human Immune Globulin In The Prophylactic Treatment Of Rabies Virus Exposure", *J. Immunological Methods*, vol. 235, 81–90, (2000).
Pluckthun, A., "Antibody Engineering: Advances From The Use Of Escherichia Coli Expression Systems", *Bio/Technology*, vol. 9, pp. 545–551, (1991).
Dietzschold, B., et al., "Biological Characterization Of Human Monoclonal Antibodies To Rabies Virus", *J. Virol.*, vol. 64, pp. 3087–3090, (1990).

* cited by examiner

*Primary Examiner*—Laurie Scheiner
(74) *Attorney, Agent, or Firm*—Drinker Biddle & Reath LLP

(57) ABSTRACT

Recombinant antibodies are disclosed. The nucleic acid and encoded amino acid sequences of the heavy and light chain immunoglobulins of human monoclonal rabies virus neutralizing antibodies, and their use, are described.

16 Claims, No Drawings

US 7,071,319 B2

RECOMBINANT ANTIBODIES, AND COMPOSITIONS AND METHODS FOR MAKING AND USING THE SAME

CROSS REFERENCE TO RELATED APPLICATIONS

This application is a continuation in part application of U.S. Ser. No. 09/848,832 filed May 4, 2001, which is incorporated herein by reference, which claims priority based upon U.S. Provisional Application No. 60/204,518, filed May 16, 2000, which is incorporated herein by reference. This application also claims priority to U.S. Provisional Application No. 60/314,023, filed Aug. 21, 2001, which is incorporated herein by reference.

FIELD OF THE INVENTION

The present invention relates to recombinant antibodies including the nucleic acid and amino acid sequence of human monoclonal rabies virus-neutralizing antibodies.

BACKGROUND OF THE INVENTION

Rabies is an acute, neurological disease caused by infection of the central nervous system with rabies virus, a member of the *Lyssavirus* genus of the family Rhabdoviridae. Of great historical significance due to its antiquity and the horrific nature of the disease, rabies virus continues to be an important threat of human and veterinary infection because of extensive reservoirs in diverse species of wildlife. Throughout much of the world, distinct variants of rabies virus are endemic in particular terrestrial animal species, with relatively little in common between them. While several islands, including the United Kingdom, Australia, Japan, and numerous islands are free of terrestrial rabies, rabies and rabies-related viruses associated with bats have recently been identified in the UK and Australia.

Rabies virus is characteristically bullet-shaped, enveloped particle of, on average, 75 by 180 nanometers. The virion consists of a single-stranded negative sense RNA genome and five structural proteins: the nucleoprotein (N) molecules, the phospho-protein (NS), the polymerase (L), the matrix protein (M) and the viral glycoprotein (G).

The N and G proteins both bear antigenic determinants which enable serotypic characterization of diverse rabies virus strains. N determinants are highly conserved between different virus isolates and are therefore very useful targets for the immunohistological detection of rabies virus infection using specific antibodies. On the other hand, antigenic determinants carried on the G-protein vary substantially among the rabies virus strains. Virus-neutralizing antibodies raised by vaccination with inactivated virus are directed against G. While it is clear that T cell responses to G, N, and NS, participate in immune responses to the virus under experimental conditions, assessment of immunity to rabies virus is generally limited to serology, particularly with respect to virus-neutralizing antibodies.

In areas of the world where human rabies is still common, the dog is the major reservoir of the viruses that infect man. Where canine rabies has largely been eliminated by vaccination, foxes, coyotes, skunks, raccoons, bats, and a variety of other mammals harbor variants of the virus. In many areas, wildlife reservoirs of virus continue to expand. Moreover, rabies virus can be transmitted from a reservoir species to humans or other end stage hosts by animals not normally associated with rabies, such as cats, rabbits, etc.

Almost invariably fatal once clinical symptoms appear, rabies can be averted by prompt treatment of an infected individual with a combination of passive and active immunization. Passive immunization consists of the administration of pre-formed rabies virus neutralizing antibodies obtained from pooled serum of rabies immune individuals (Human rabies-immune globulin; HRIG) or hyper-immunized horses (Equine rabies-immune globulin; ERIG). Both types of reagent present certain risks to recipients including variable antigen specificity, and thus potency, for different rabies virus isolates.

HRIG is prepared from pooled human sera, therefore there is the possibility that HRIG preparations could be contaminated with known or unknown human pathogens. On the other hand, as a preparation of foreign antigen, ERIG has been associated with severe anaphylactic reactions. Mouse monoclonals specific for rabies virus have been contemplated for use in post-exposure prophylaxis but, like ERIG, are antigenically foreign to humans. This may result in their rapid clearance from the human system, as well as the potential to cause an anaphylactic reaction.

The use of human monoclonal antibodies is limited since human hybridoma cell lines are hard to prepare, generally unstable, and do not produce monoclonal antibodies of appropriate specificity in sufficient quantities and at reasonable costs. Production costs of monoclonal antibodies make it desirable to find more economic alternatives to obtaining monoclonal antibodies from hybridomas.

It is well established that both the Fab and Fab2 regions, which comprise the variable and hinge regions of the heavy and light chains, do not protect against rabies virus infection. The in vivo efficacy of the antibody relies on the entire sequence, that is only particular antibodies exhibit anti-rabies activity. It is the constant region of the antibody that is responsible for immunoreactivity. Thus, it is particular attributes of the constant region(s) that are required to protect against the rabies virus. Variable regions spliced to a constant region of another antibody, that is an antibody that is not naturally made against the rabies virus, are ineffective.

There is a need for recombinant antibodies useful in the diagnosis, prevention and treatment of rabies infection, and pharmaceutical compositions that comprise and methods that use the same. There is a need for compositions and methods for producing such recombinant antibodies.

There is a need for recombinant antibodies useful in the diagnosis, prevention and treatment of infection of pathogens that target neuronal tissue, and pharmaceutical compositions that comprise and methods that use the same. There is a need for compositions and methods for producing recombinant antibodies.

To provide a better reagent, human monoclonal antibodies have been made by fusion of Epstein-Barr Virus (EBV)-transformed, rabies virus-specific human B cells with mouse-human heterohybrid donors. cDNA clones encoding the antibody heavy and light chains from these cells were constructed such that the antibodies were expressed in heterologous expression systems. These constructs allow rabies neutralizing human antibodies of defined specificity to be produced in a controlled system, purified away from possible deleterious contaminants. The present invention relates to these monoclonal rabies virus neutralizing human antibodies, the nucleic acid sequences of their heavy and light chains and the amino acid sequences of the encoded proteins. Also provided in the present invention are methods of using the monoclonal antibodies as a therapeutically effective post-exposure prophylactic treatment of individuals exposed to rabies virus.

SUMMARY OF THE INVENTION

The present invention provides recombinant antibodies, and compositions for and methods of producing such antibodies. According to some aspects of the invention, the present invention provides recombinant anti-rabies antibodies, and compositions for and methods of producing such antibodies. According to some aspects of the invention, the present invention provides recombinant antibodies with a specific constant region that makes them particularly effective in combating pathogens which attack the neural system.

The present invention further relates to isolated DNA sequences, to recombinant vectors comprising such sequences, to host cells comprising such vectors and methods of producing recombinant antibodies using such host cells.

The present invention additionally relates to the use of recombinant antibodies in the diagnosis, prevention and treatment of pathogen infections of neuronal tissue, particularly rabies.

The present invention provides isolated nucleic acid molecules having a heavy chain and a light chain nucleic acid sequence encoding a heavy chain and a light chain amino acid sequence. The heavy chain and light chain amino acid sequences are that of a monoclonal rabies virus neutralizing antibody that specifically binds to a rabies virus protein.

The present invention provides isolated nucleic acid molecules that encode the monoclonal rabies virus neutralizing antibody are derived from cDNA sequences of the heavy chain SEQ. ID. NO:1 and the light chain SEQ. ID. NO:2.

The present invention provides an isolated human monoclonal rabies virus neutralizing antibody that is encoded in CDNA clones encoding the antibody heavy and light chains expressed in heterologous expression systems and purified away from deleterious contaminants. In one embodiment of the present invention the amino acid sequence of the isolated human monoclonal rabies virus neutralizing antibody is that of the SEQ. ID. NO:3 and SEQ. ID. NO:4, respectively.

The present invention provides a fused gene encoding a chimeric immunoglobulin light chain. The chimeric light chain contains a first DNA sequence encoding an immunoglobulin light chain variable region of a monoclonal rabies virus neutralizing antibody produced by a heterohybridoma cell line; and a second DNA sequence encoding a human light chain constant region. The present invention provides an expression vector to express this fused gene. It is a further object to provide a host cell for the expression vector.

The present invention provides a fused gene encoding a chimeric immunoglobulin heavy chain. The chimeric heavy chain contains a first DNA sequence encoding an immunoglobulin heavy chain variable region of a monoclonal rabies virus neutralizing antibody produced by a heterohybridoma cell line; and a second DNA sequence encoding a human heavy chain constant region. It The present invention provides an expression vector to express this fused gene. It is a further object to provide a host cell for the expression vector.

The present invention provides an isolated monoclonal rabies virus neutralizing antibody derived from the fused gene encoding a chimeric immunoglobulin light chain and the fused gene encoding a chimeric immunoglobulin heavy chain.

The present invention provides a method of treating an individual exposed to a rabies virus by administering to the individual a therapeutically effective amount of a human monoclonal rabies virus neutralizing antibody that is encoded in cDNA clones encoding the antibody heavy and light chains expressed in heterologous expression systems and purified away from deleterious contaminants, thereby preventing the spread of rabies virus to the central nervous system.

DESCRIPTION OF THE INVENTION

The present invention provides monoclonal antibodies that bind specifically to the glycoprotein of various rabies virus strains. Post-exposure treatment with monoclonal antibody, or a mixture of a variety of monoclonal antibodies, will neutralize the rabies virus at the site of entry and prevent the virus from spreading to the central nervous system (CNS). Thus, for transdermal or mucosal exposure to rabies virus, rabies specific-monoclonal antibodies are instilled into the bite site, as well as administered systemically. Since viral replication is restricted almost exclusively to neuronal cells, neutralization and clearance of the virus by the monoclonal antibodies of the present invention prior to entry into the CNS is an effective post-exposure prophylactic.

One aspect of the present invention provides sequences of monoclonal antibodies against rabies virus. While most of the variable region of MAb 57 is well known (Cheung et al., *J. Virol.* 66:6714–6720, 1992, which is incorporated herein by reference), the constant region is not. The entire monoclonal antibody, both constant and variable regions, has been cloned and sequenced. The present invention provides the novel nucleotide sequence of MAb 57 constant region, nucleotides 476–1431, which includes constant domain 1 (CH1) and the hinge region. This sequence may be used in recombinant antibodies including anti-rabies antibodies or recombinant antibodies directed at other pathogens which attack neuronal tissue, such as encephalitis or herpes.

The invention relates to the recombinant antibodies, to the clones genes that encode them, to the vectors which incorporate cloned genes and host cells that include the vectors. The invention also provides methods of making and using the recombinant antibodies.

The present invention provides recombinant antibodies derived from MAb 57. MAb 57 derived from hybridomas are IgG2 antibodies; recombinant antibodies derived from MAb 57 are IgG1 antibodies. The invention relates to the recombinant antibodies derived from Mab 57, to the clones genes that encode them, to the vectors which incorporate cloned genes and host cells that include the vectors. The invention also provides methods of making and using the recombinant antibodies.

The present invention also provides the entire sequence of the heavy and light chains of the anti-rabies monoclonal antibody MAb JA. The invention relates to the recombinant antibodies derived from Mab JA, to the clones genes that encode them, to the vectors which incorporate cloned genes and host cells that include the vectors. The invention also provides methods of making and using the recombinant antibodies.

The present invention also provides the entire sequence of the heavy and light chains of the anti-rabies monoclonal antibody MAb JB.1. The invention relates to the recombinant antibodies derived from Mab JB.1, to the clones genes that encode them, to the vectors which incorporate cloned genes and host cells that include the vectors. The invention also provides methods of making and using the recombinant antibodies.

According to some embodiments, the recombinant antibody of the invention is a single-chain antibody wherein the heavy chain variable domain and the light chain variable domain are linked by way of a spacer group, preferably a peptide. Most preferred is a single-chain antibody wherein the heavy chain variable domain is located at the N-terminus of the recombinant antibody. The single-chain recombinant antibody may further comprise an effector molecule and/or signal sequences facilitating the processing of the antibody by the host cell in which it is prepared.

The recombinant antibodies of the invention can be used to identify rabies virus such as by immunofluorescent staining of infected cells, by immunoblotting either directly or by way of immunoprecipition and protein blotting of the immunocomplexes, or by another immunoassay such as a binding, crossinhibition or competition radio- or enzyme immunoassay.

The invention further concerns a method of manufacture of the recombinant antibodies of the invention. The recombinant antibodies of the invention can be prepared by recombinant DNA techniques comprising culturing a transformed host under conditions which allow expression thereof and isolating said antibody.

More specifically, the present invention also relates to a process for the production of a recombinant antibody comprising culturing a host which has been transformed with a hybrid vector comprising an expression cassette comprising a promoter and a DNA coding for said recombinant antibody which DNA is controlled by said promoter, and isolating said recombinant antibody.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly E. coli, to obtain an optimal expression of the recombinant antibody.

Furthermore the invention concerns a recombinant DNA which is a hybrid vector comprising an insert coding for the recombinant antibody described hereinbefore, and, optionally an origin of replication or an autonomously replicating sequence, one or more dominant marker sequences, expression control sequences, signal sequences and additional restriction sites.

Vectors typically perform two functions in collaboration with compatible host cells. One function is to facilitate the cloning of the nucleic acid that encodes the immunoglobulin domains, i.e. to produce usable quantities of the nucleic acid (cloning vectors). The other function is to provide for replication and expression of the recombinant gene constructs in a suitable host, either by maintenance as an extrachromosomal element or by integration into the host chromosome (expression vectors). A cloning vector comprises the recombinant gene constructs as described above, an origin of replication or an autonomously replicating sequence, dominant marker sequences and, optionally, signal sequences and additional restriction sites. An expression vector additionally comprises expression control sequences essential for the transcription and translation of the recombinant genes.

An origin of replication or an autonomously replicating sequence is provided either by construction of the vector to include an exogenous origin such as derived from Simian virus 40 (SV 40) or another viral source, or by the host cell chromosomal mechanisms.

The markers allow for selection of host cells which contain the vector. Selection markers include genes which confer resistance to heavy metals such as copper or to antibiotics such as geneticin (G-418) or hygromycin, or genes which complement a genetic lesion of the host cell such as the absence of thymidin kinase, hypoxanthine phosphoryl transferase, dihydrofolate reductase or the like.

Signal sequences may be, for example, presequences or secretory leaders directing the secretion of the recombinant antibody, splice signals, or the like. Examples for signal sequences directing the secretion of the recombinant antibody are sequences derived from the ompA gene, the pelB (pectate lyase) gene or the phoA gene.

As expression control sequences, the vector DNA comprises a promoter, sequences necessary for the initiation and termination of transcription and for stabilizing the mRNA and, optionally, enhancers and further regulatory sequences.

A wide variety of promoting sequences may be employed, depending on the nature of the host cell. Promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host. Enhancers are transcription-stimulating DNA sequences of viral origin, e.g. derived from Simian virus, polyoma virus, bovine papilloma virus or Moloney sarcoma virus, or of genomic, especially murine, origin.

The various DNA segments of the vector DNA are operationally linked, i.e. they are contiguous and placed into a functional relationship with each other. Examples of vectors which are suitable for replication and expression in an E. coli strain are bacteriophages, for example derivatives of .lambda. bacteriophages, or plasmids, such as, in particular, the plasmid ColE1 and its derivatives, for example pMB9, pSF2124, pBR317 or pBR322 and plasmids derived from pBR322, such as pUC9, pUCK0, pHRi148 and pLc24. Suitable vectors contain a complete replicon, a marker gene, recognition sequences for restriction endonucleases, so that the foreign DNA and, if appropriate, the expression control sequence can be inserted at these sites, and optionally signal sequences and enhancers.

Microbial promoters are, for example, the strong leftward promoter $P_L$ of bacteriophage λ. which is controlled by a temperature sensitive repressor. Also suitable are E. coli promoters such as the lac (lactose) promoter regulated by the lac repressor and induced by isopropyl-.beta.-D-thiogalactoside, the trp (tryptophan) promoter regulated by the trp repressor and induced e.g. by tryptophan starvation, and the tac (hybrid trp-lac promoter) regulated by the lac repressor.

Vectors which are suitable for replication and expression in yeast contain a yeast replication start and a selective genetic marker for yeast. One group of such vectors includes so-called ars sequences (autonomous replication sequences) as origin of replication. These vectors are retained extrachromosomally within the yeast cell after the transformation and are replicated autonomously. Furthermore, vectors which contain all or part of the 2 μm plasmid DNA from Saccharomyces cerevisiae can be used. Such vectors will get integrated by recombination into 2 μm plasmids already existing within the cell, or replicate autonomously. 2 μm sequences are particularly suitable when high transformation frequency and high copy numbers are to be achieved.

Expression control sequences which are suitable for expression in yeast are, for example, those of highly expressed yeast genes. Thus, the promoters for the TRP1 gene, the ADHI or ADHII gene, acid phosphatase (PHO3 or PHO5) gene, isocytochrome gene or a promoter involved with the glycolytic pathway, such as the promoter of the enolase, glyceraldehyde-3-phosphate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, can be used.

Vectors suitable for replication and expression in mammalian cells are preferably provided with promoting sequences derived from DNA of viral origin, e.g. from Simian virus 40 (SV40), Rous sarcoma virus (RSV), adenovirus 2, bovine papilloma virus (BPV), papova-virus BK mutant (BKV), or mouse or human cytomegalovirus (CMV). Alternatively, the vectors may comprise promoters from mammalian expression products, such as actin, collagen, myosin etc., or the native promoter and control sequences which are normally associated with the desired gene sequence, i.e. the immunoglobulin H-chain or L-chain promoter.

Some preferred vectors are suitable for both procaryotic and eucaryotic hosts and are based on viral replication systems. Particularly preferred are vectors comprising Simian virus promoters, e.g. pSVgpt or pSVneo, further comprising an enhancer, e.g. an enhancer normally associated with the immunoglobulin gene sequences, in particular the mouse Ig H- or L-chain enhancer.

The recombinant DNA coding for a recombinant antibody of the invention can be prepared, for example, by culturing a transformed host cell and optionally isolating the prepared DNA.

Moreover, the invention relates to host cells transformed with the recombinant DNAs described above, namely host cells which are transformed with a DNA encoding the heavy chain and/or a DNA encoding the light chain of the desired recombinant antibody, in particular host cells transformed with a DNA encoding the single-chain recombinant antibody.

More specifically, the invention concerns a host cell which has been transformed with a hybrid vector comprising an expression cassette comprising a promoter and a DNA coding for a recombinant antibody.

Furthermore, the invention pertains to a host cell which has been transformed with a hybrid vector comprising an expression cassette comprising a promoter operably linked to a first DNA sequence encoding a signal peptide linked in the proper reading frame to a second DNA sequence encoding a recombinant antibody.

Examples of suitable hosts are microorganisms which are devoid of or poor in restriction enzymes or modification enzymes, such as bacteria, in particular strains of *Escherichia coli*, for example *E. coli* X1776, *E. coli* Y1090, *E. coli* HB 101, *E. coli* W3110, *E. coli* HB 101/LM1035, *E. coli* JA 221, *E. coli* DH5.alpha., *E. coli* K12, or *E. coli* CC118 strain, *Bacillus subtilis, Bacillus stearothermophilus, Pseudomonas, Haemophilus, Streptococcus* and others, and yeasts, for example *Saccharomyces cerevisiae* such as *S. cerevisiae* GRF 18. Further suitable host cells are cells of higher organisms, in particular established continuous human or animal cell lines, e.g. human embryonic lung fibroblasts L132, human malignant melanoma Bowes cells, HeLa cells, SV40 virus transformed kidney cells of African green monkey COS-7 or Chinese hamster ovary (CHO) cells, or cells of lymphoid origin, such as lymphoma, myeloma, hybridoma, trioma or quadroma cells, for example PAI, Sp2/0 or X63-Ag8.653 cells.

The invention also concerns processes for the preparation of transformed host cells wherein suitable recipient host cells as described hereinbefore are transformed with a hybrid vector according to the invention, and the transformed cells are selected. Transformation of microorganisms is carried out as described in the literature, for example for *S. cerevisiae* (A. Hinnen et al., Proc. Natl. Acad. Sci. USA 75: 1929, 1978), for *B. subtilis* (Anagnostopoulos et al., J. Bacteriol. 81: 741, 1961), and for *E. coli* (M. Mandel et al., J. Mol. Biol. 53: 159, 1970).

Accordingly, the transformation procedure of *E. coli* cells includes, for example, $Ca^{2+}$ pretreatment of the cells so as to allow DNA uptake, and incubation with the hybrid vector. The subsequent selection of the transformed cells can be achieved, for example, by transferring the cells to a selective growth medium which allows separation of the transformed cells from the parent cells dependent on the nature of the marker sequence of the vector DNA. Preferably, a growth medium is used which does not allow growth of cells which do not contain the vector. The transformation of yeast comprises, for example, steps of enzymatic removal of the yeast cell wall by means of glucosidases, treatment of the obtained spheroplasts with the vector in the presence of polyethylene glycol and $Ca^{2+}$ ions, and regeneration of the cell wall by embedding the spheroplasts into agar. Preferably, the regeneration agar is prepared in a way to allow regeneration and selection of the transformed cells as described above at the same time.

Transformation of cells of higher eucaryotic origin, such as mammalian cell lines, is preferably achieved by transfection. Transfection is carried out by conventional techniques, such as calcium phosphate precipitation, microinjection, protoplast fusion, electroporation, i.e. introduction of DNA by a short electrical pulse which transiently increases the permeability of the cell membrane, or in the presence of helper compounds such as diethylaminoethyldextran, dimethyl sulfoxide, glycerol or polyethylene glycol, and the like. After the transfection procedure, transfected cells are identified and selected, for example, by cultivation in a selective medium chosen depending on the nature of the selection marker, for example standard culture media such as Dulbecco's modified Eagle medium (DMEM), minimum essential medium, RPMI 1640 medium and the like, containing e.g. the corresponding antibiotic.

The recombinant antibodies according to the invention can be used for the qualitative and quantitative determination of the presence of rabies virus. In general, the recombinant antibodies according to the invention can be used in any of the known immunoassays which rely on the binding interaction between the antibodies and rabies antigens. Examples of such assays are radio-, enzyme, fluorescence, chemiluminescence, immunoprecipitation, latex agglutination, and hemagglutination immunoassays, and, in particular, immunostaining methods.

The antibodies according to the invention can be used as such or in the form of enzyme-conjugated derivatives in an enzyme immunoassay. Any of the known modifications of an enzyme immunoassay can be used, for example soluble phase (homogeneous) enzyme immunoassay, solid phase (heterogeneous) enzyme immunoassay, single enzyme immunoassay or double (sandwich) enzyme immunoassay with direct or indirect (competitive) determination of the presence of rabies virus.

An example of such an enzyme immunoassay is a sandwich enzyme immunoassay in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with a monoclonal antibody of the invention by simple adsorption or optionally after activation of the carrier, for example with glutaraldehyde or cyanogen bromide. Then test solutions containing the rabies virus and finally recombinant antibodies of the invention comprising a detectable enzyme, e.g. alkaline phosphatase, are added. The amount of the rabies virus in the test solution is directly proportional to the amount of bound recombinant antibody and is determined by adding an enzyme substrate solution. The enzyme substrate reaction results, for example, in a color change which can be observed by eye or with optical measuring devices.

The antibodies according to the invention can be used as such or in the form of radioactively labelled derivatives in a radioimmunoassay (RIA). As described above for enzyme immunoassays, any of the known modifications of a radioimmunoassay can be used.

The tests are carried out in an analogous manner to the enzyme immunoassays described above using a radioactive label, e.g. $^{125}I$, instead of an enzyme label. The amount of immune complex formed which corresponds to the amount of rabies virus present in the test solutions is determined by measuring the radioactivity of the immune complex.

For immunostaining cryosections of cryopreserved biopsy material or paraffin embedded tissue sections are treated with a solution containing a recombinant antibody of the invention comprising a detectable enzyme. Bound recombinant antibody is detected by treatment with a suitable enzyme substrate, preferably an enzyme substrate which leads to a solid deposit (stain) at the site of the recombinant antibody of the invention. In place of recombinant antibodies comprising an enzyme, a recombinant antibody comprising streptavidin and a solution of a biotin-enzyme-conjugate may be used, which leads to higher enzyme concentration at the site of the antibody and hence increased sensitivity of the immunostaining method. The solid deposit of the enzyme substrate is detected by inspection with a microscope, for example with a fluorescence microscope, or by scanning the optical density at the wavelength of the stain.

The use according to the invention of recombinant antibodies as described hereinbefore for the determination of rabies virus also includes other immunoassays known per se, for example immunofluorescence assays, latex agglutination with antibody-coated or antigen coated latex particles, hemagglutination with antibody-coated or antigen-coated red blood corpuscles, evanescent light assays using an antibody-coated optical fibre and other direct-acting immunosensors which convert the binding event into an electrical or optical signal, or the like.

The invention also concerns test kits for the qualitative and quantitative determination of presence of rabies virus comprising recombinant antibodies of the invention and, optionally, adjuncts, positive and/or negative controls, buffers, instructions and descriptions of exemplary results.

Furthermore, the recombinant antibodies of the invention, in are useful for the prevention of rabies infection in patients suspected of possible exposure to rabies virus or the treatment of patients who have been infected with rabies.

The invention therefore also concerns pharmaceutical compositions comprising a therapeutically effective amount of a recombinant antibody according to the invention and a pharmaceutically acceptable carrier. Preferred are pharmaceutical compositions for parenteral application. Compositions for intramuscular, subcutaneous or intravenous application are e.g. isotonic aqueous solutions or suspensions, optionally prepared shortly before use from lyophilized or concentrated preparations. Suspensions in oil contain as oily component the vegetable, synthetic or semi-synthetic oils customary for injection purposes. The pharmaceutical compositions may be sterilized and contain adjuncts, e.g. for conserving, stabilizing, wetting, emulsifying or solubilizing the ingredients, salts for the regulation of the osmotic pressure, buffer and/or compounds regulating the viscosity, e.g. sodium carboxycellulose, carboxymethylcellulose, sodium carboxymethylcellulose, dextran, polyvinylpyrrolidine or gelatine.

The pharmaceutical compositions of the invention contain from approximately 0.01% to approximately 50% of active ingredients. They may be in dosage unit form, such as ready-to-use ampoules or vials, or also in lyophilized solid form.

In general, the prophylactically and therapeutically effective doses for mammals is between approximately 0.5 and 250 μg of a recombinant antibody of the invention per kg body weight depending on the type of antibody, the status of the patient and the mode of application. The specific mode of administration and the appropriate dosage will be selected by the attending physician taking into account the particulars of the patient, the state of the disease, the type of tumor treated, and the like. The pharmaceutical compositions of the invention are prepared by methods known in the art, e.g. by conventional mixing, dissolving, confectioning or lyophilizing processes. Pharmaceutical compositions for injection are processed, filled into ampoules or vials, and sealed under aseptic conditions according to methods known in the art.

In some embodiments the compositions and/or, methods relate to antibody cocktails in which one or more antibodies are combined. In preferred embodiments, the cocktails contain two or more antibodies of the present invention.

EXAMPLE

Example 1

Cells

The human B cells used for hybridization were obtained from the peripheral blood of 5 donors between 7 and 21 days after the third dose of a primary rabies vaccination and 5 rabies-immune donors 10 to 21 days following administration of booster vaccine. In all cases the vaccine employed was Rabivac™ human diploid cell vaccine (virus strain Pitman Moore 1503-3M, Behringwerke, Marburg, FRG). All of the donors were negative in tests for HIV and hepatitis B. The mouse-human hybrid heteromyeloma SHM-D33 cells utilized as hybridoma fusion partners (Teng, N. N. et al., *Proc. Natl. Acad. Sci. USA* 80, 7308, 1983) and B95-8 Epstein-Barr Virus (EBV)-transformed marmoset leukocytes used as a source of EBV (Henderson et al., *J. Exp. Med.* Vol 76, p. 152, 1977) were obtained from ATCC (Rockville, Md.).

Rabies Viruses

To assess the capacity of antibody preparations to neutralize a variety of rabies virus strains, a number of antigenically distinct fixed, laboratory strains, as well as two representative street rabies viruses, were used. Evelyn-Rokitnicki-Abelseth (ERA), challenge virus standard, either mouse brain adapted (CVS-24) or cell culture adapted (CVS-11), and Pitman-Moore (PM) fixed strains were obtained from the Thomas Jefferson University virus collection. Silver-haired bat rabies virus (SHBRV), which has been associated with most of the recent rabies cases in the United States of America, and coyote street rabies virus/Mexican dog rabies virus (COSRV), which is a member of the dog rabies viruses, were obtained as described (Morimoto et al., *Proc. Natl. Acad. Sci. USA,* Vol. 93, p. 5653, 1996). Virus purification and preparation of glycoprotein (G) and nucleoprotein (N) have been described elsewhere (Dietzschold et al., *World Health Organization,* Geneva, p. 175, 1996).

EBV-Transformation of Human PBLs

Peripheral blood mononuclear cells (PBMCs) were isolated from whole blood by density centrifugation on Ficoll-Paque (Amersham Pharmacia Biotech, Piscataway, N.J.) as detailed elsewhere (Plebanski et al., Immunology Vol. 75, p. 86, 1992). T cells were then depleted by negative selection using monoclonal anti-CD2 antibody-coated magnetic beads (Dynal Inc., Lake Success N.Y.) and a magnetic particle concentrator (Dynal). CD-2-negative cells, primarily B cells, were collected and immortalized as previously described (Swaminathan, 1992). Briefly, B95-8 cells, cultured to confluency in $RPMI_{1640}$ (Gibco BRL Life Technologies, Grand Island N.Y.) supplemented with 10% fetal bovine serum (FBS; Gibco), were lysed by freeze-thawing on dry ice to release intracellular EBV. Supernatant containing EBV was clarified by spinning at 1000 RPM for 10 min and by filtration through a 0.45 μm filter. Virus was concentrated by centrifugation at 8000 RPM for 2 h at 4° C. $7 \times 10^6$ B cells (suspended in 1 ml of B95-8 culture media) were incubated at 37° C. for 2 h with virus prepared from 25 mls of B95-8 cells. Following infection, the cells were washed twice with culture media, plated in 96 well flat-bottom microtiter plates (Nunc, Fisher Scientific, Pittsburgh, Pa.) at a concentration of $1 \times 10^4$ cells/well, and cultured at 37° C. in a humidified atmosphere of 5% $CO_2$ and 95% air.

Establishment of Mouse-Human Hetereohybrids

After the EBV-transformed cell lines had been cultured for approximately 4 weeks, supernatant was harvested and tested for the presence of rabies virus-specific antibody in ELISA. Positive wells were transferred first to 1 ml and then to 2 ml cultures (48 and 24 well plates, Nunc) and the supernatant then assayed in the rapid fluorescent focus inhibition test (RFFIT) for rabies virus neutralizing antibody, as detailed elsewhere (Hooper, *ASM Press, WA* p. 755, 1997). Cell lines producing neutralizing antibody were hybridized with SHM-D33 cells (ATCC Accession Number CRL1668) as follows. Equal numbers of SHM-D33 and EBV-transformed cells (approximately $5 \times 10^6$ each) were added together into a sterile polystyrene round-bottom tube (Falcon, Fisher Scientific) and centrifuged at 1000 RPM for 10 min. Cells were washed twice with serum-free medium and the cell pellet resuspended in 100 μl of medium.

Tubes were warmed in a 37° C. water bath for 1 min and then 0.5 ml of warm (37° C.) 50% (wt/vol) polyethylene glycol (Sigma Chemical Co., St. Louis, Mo., cat. #P-7181) was added, dropwise over a 45-sec period while gently shaking the tube. The fusion reaction was then stopped by the slow addition of 3 ml of serum-free medium over 30 sec followed by the addition of 9 ml over 30 sec. The tubes were allowed to stand at room temperature for 8 min and then incubated for 2 min in a 37° C. water bath. The cells were then centrifuged at 500 g for 3 min and the cell pellet gently resuspended in 30 ml of Iscove's modification of Dulbecco's (IMDM; Gibco) medium containing 10% FBS, as well as 0.04 μM aminopterin (Gibco) and 10 μM oubain (Sigma) to select against cells which had not hybridized. Cell suspensions were plated in 96 well flat-bottom microtiter plates at a concentration of $1 \times 10^4$ cells per well and incubated as described for the lines.

When colonies of heterohybrid cells had become established (approximately 6 weeks of culture) supernatants were tested for rabies virus-specific antibody production in ELISA and RFFIT. Antibody-producing cells were cloned a minimum of three times by limiting dilution in microtiter plates. Cells were titrated in 96 well round bottom plates in 2-fold dilutions starting from 4 cells per well. Cells from wells containing an average of 0.25 cells or less were expanded for the collection of supernatant and further analysis.

Analysis of Rabies Virus-Specific Antibodies in ELISA

Antibody specificity and isotype was assessed in solid phase ELISA. Plates (PolySorb™, Nunc) were coated at room temperature in a humidified chamber overnight with 5*g/ml rabies ERA virus, glycoprotein, or nucleoprotein diluted in phosphate-buffered saline (PBS). The plates were then blocked with 5% powdered milk in PBS and washed in PBS containing 0.05% $Tween_{20}$ (PBS-Tween) prior to the addition of supernatant samples.

Following incubation at room temperature for 2 h, the plates were washed with PBS-Tween to remove unbound primary antibody and various enzyme-conjugated or biotinylated secondary antibodies specific for the various human heavy chain isotypes were added for 1 h at room temperature. Secondary antibody was detected either by the production of a soluble end product in the medium upon addition of the appropriate substrate (3,3',5,5'-tetramethylbenzidine (TMB) in phosphate-citrate buffer, or p-nitrophenyl phosphate (PNPP) in 0.1 Mglycine buffer, Sigma) or following the addition of avidin-alkaline phosphatase (30 min at RT) and PNPP substrate. The peroxidase-TMB reaction was stopped bye the addition of 2M $H_2SO_4$. Absorbance values were read in a microplate spectrophotometer (Biotek, Winooski Vt.) at 450 nm for the TMB product and at 405 nm for the PNPP reaction.

RFFIT

Supernatant samples from each transformed cell line were assayed for the presence of rabies virus-neutralizing antibodies using a variation of the rapid fluorescent focus inhibition test (RFFIT) as previously described (Hooper, ASM Press, WA p. 1997). Supernatant samples (50 μl) were diluted in 96 well flat-bottom plates (Nunc). Rabies virus dilution known to cause 80–90% infection of the indicator cells were added to each test sample, and the plates incubated at 37° C. for 1 h. Negative media and positive rabies-immune serum control samples were included in each assay. After incubation, 30 ul of a $1.8 \times 10^6$ cells/ml concentration of baby hamster kidney (BHK) cells were added to each well and cultures incubated overnight at 37° C. The plates were then washed once with ice-cold PBS and fixed with ice-cold 90% acetone for 20 min at −20° C. After fixation, acetone was removed and the plates were air dried. To detect infected BHK cells, 40 ul of FITC anti-rabies nucleoprotein monoclonal globulin (Centocor, Malvern Pa.) were added to each well for 45 min at 37° C. The plates were then washed three times with distilled water and examined under a fluorescent microscope.

Purification of Antibodies by Affinity Chromatography

IgG1 antibody was purified using a protein A column (rProtein A Sepharose™ Fast Flow, Amersham Pharmacia Biotech). Briefly, supernatants were clarified by filtration through a 0.45 μm membrane and the pH adjusted to 8.0 with 1N NaOH. Supernatant was run through the column at a linear flow rate of approximately 100 cm/hour. After washing in PBS (pH 8), antibody was eluted from the column using a 0.1M citric acid solution and then dialyzed against PBS.

IgG3 antibody was purified using a protein G column (Protein G Sepharose™ Fast Flow, Amersham Pharmacia Biotech). IgG3-containing supernatant was clarified by filtration through a 0.45 μm membrane and the pH adjusted to 7.0 with 1N NaOH. Supernatant was run through the column at a linear flow rate of approximately 11 cm/hour. After washing with PBS, antibody was eluted from the column using 0.1M glycine buffer, pH 3.0, and then dialyzed against PBS.

IgM antibody was purified using mannan binding protein and a modification of a previously described technique (Nevens et al., *J. Chromatogr,* Vol. 597, p. 247, 1992). Briefly, supernatant containing IgM was EDTA treated, brought to pH 8.0 with 1M NaOH, filtered and cooled to 4° C. Mannan binding protein-agarose (Sigma) was washed in a column at 4° C. with buffer consisting of 0.1M Na**CO$_3$/0.5M NaCl, pH 8.3 and then the supernatant was added and incubated on the column for 15 min at 4° C. The column was then washed with several volumes of binding buffer and brought to RT for 1 h. The IgM was eluted from the column with binding buffer at RT and dialyzed against PBS.

Protein concentrations of the dialyzed antibody preparations were determined using a protein detection assay (Bio-Rad Laboratories, Hercules Calif.) as follows. 100 μl of sample were added to 5 ml of a 1/5 dilution of dye reagent concentrate and incubated at RT for 10 minutes. Negative PBS control and various bovine serum albumin (BSA) protein standards were included in each assay. After incubation, samples were read in a spectrophotometer at 595 nm. Protein concentrations of test samples were calculated with reference to the absorbance of the BSA standards. The purity of all antibody preparations was assessed by electrophoresis in 12.5% polyacrylamide gel under reducing conditions (SDS-PAGE). Purified antibodies showed two major bands on SDS-PAGE corresponding to isolated heavy and light immunoglobulin chains.

Generation, Isolation and Sequencing of cDNA Clones

Total RNA was isolated from JA hybridoma cell by using RNAzol B (Biotecx Laboratories, Houston). Reverse transcriptase reactions were performed at 42° C. for 1 hr with avian myeloblastosis virus reverse transcriptase (Promega) and oligo(dT) primer. A portion of the reverse transcriptase products were subjected to polymerase chain reaction (PCR) amplification using heavy chain specific primers: IgG-HF1 primer (5'-ACC<u>ATG</u>GAGTTTGGGCTGAG-3' (SEQ. ID. NO: 5), start codon; underline, accession #Y14737), and IgG-HR2 primer (5'-AC<u>TCA</u>TTTACCCGGGGACAG-3' (SEQ. ID. NO: 6), stop codon; underline, accession #Y14737) or light chain specific primers: IgG-LF5 primer (5'-AGC<u>ATG</u>GAAGCCCCAGCTCA-3' (SEQ. ID. NQ: 7), start codon; underline, accession #M63438), and IgG-LR2 primer (5'-CT<u>CTA</u>ACACTCTCCCCTGTTG-3' (SEQ. ID. NO: 8), stop codon, underline accession #M63438). Amplification was carried out for 35 cycles of denaturation at 94° C. for 60 seconds, annealing at 50° C. for 60 seconds, and polymerization at 72° C. for 90 seconds with Taq DNA polymerase (Promega). The PCR products (1.4 kb for heavy chain, 0.7 kb for light chain) were purified and sequenced by using the AmpliTaq cycle sequencing kit (Perkin-Elmer) with the specific primers. The PCR products were cloned into TA cloning vector, pCR2.1 (Invitrogen). The cloned heavy chain and light chain cDNA was sequenced by using the AmpliTaq cycle sequencing kit (Perkin-Elmer) with the specific primers.

Monoclonal Rabies Virus Neutralizing Antibody Coding Sequences

Monoclonal antibody cDNA, and sequences complementary thereto, are monoclonal antibody nucleic acids provided by the present invention. In a specific embodiment herein, a monoclonal antibody cDNA sequence is provided for the heavy chain (SEQ. ID. NO:1) and the light chain (SEQ. ID. NO:2) of the monoclonal antibody from clone JA, thus lacking any introns.

The invention also provides single-stranded oligonucleotides for use as primers in PCR that amplify a monoclonal antibody sequence-containing fragment, for example the variable or hypervariable region of the monoclonal antibody. The oligonucleotide having the sequence of a hybridizable portion, at least 8 nucleotides, of a monoclonal antibody gene, and another oligonucleotide having the reverse complement of a downstream sequence in the same strand of the monoclonal antibody gene, such that each oligonucleotide primes synthesis in a direction toward the other. The oligonucleotides are preferably in the range of 10–35 nucleotides in length.

The present invention provides the full-length cDNA sequences for the heavy and light chains of the monoclonal antibody of heterohybridoma clone JA (SEQ. ID. NO:1 and SEQ. ID NO:2, respectively), and the encoded polypeptides of #1-474 amino acids for the heavy chain (SEQ. ID. NO:3) and #1-234 amino acids for the light chain (SEQ. ID. NO:4).

In a specific embodiment disclosed herein, the invention relates to the nucleic acid sequence of the monoclonal antibody from heterohybridoma clone JA. In a preferred, but not limiting, aspect of the invention the heterohybridoma clone JA is the source of the monoclonal antibody cDNA.

Functional Equivalents of Monoclonal Rabies Virus Neutralizing Antibodies

The invention also includes functional equivalents of the antibodies described in this specification. Functional equivalents have binding characteristics comparable to those of the antibodies, and include, for example, chimerized and single chain antibodies, as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Functional equivalents include polypeptides with amino acid sequences substantially the same as the amino acid sequence of the variable of hypervariable regions of the antibodies of the present invention. "Substantially the same" amino acid sequence is defined herein as a sequence with at least 70%, preferably at least about 80%, and more preferably at least about 90% homology to another amino acid sequence, as determined by the FASTA search method in accordance with Pearson and Lipman, *Proc. Natl. Inst. Acad. Sci. USA* 85, 2444–2448, 1988. Chimerized antibodies have constant regions derived substantially or exclusively from human antibody constant regions and variable regions derived substantially or exclusively from the sequence of the variable region of a monoclonal antibody from each stable heterohybridoma (Champion, J. M., et al., *Journal of Immunological Methods,* 235 81–90, 2000).

Single chain antibodies or Fv fragments are polypeptides that consist of the variable region of the heavy chain of the antibody linked to the variable region of the light chain, with or without an interconnecting linker. Thus, the Fv comprises the entire antibody combining site.

Functional equivalents further include fragments of antibodies that have the same, or substantially the same, binding characteristics to those of the whole antibody. Such fragments may contain one or both Fab fragments of the F(ab').sub.2 fragment. Preferably the antibody fragments contain all the s*complement of determining region of the whole antibody, although fragments containing fewer than all of such regions, such as three, four or five complement determining regions, are also functional. The functional equivalents are members of the IgG immunoglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, chimeric antibodies with desired effector function are produced. Preferred constant regions are gamma 1 (IgG1), gamma 3 (IgG3) and gamma 4 (IgG4). The light chain constant region can be of the kappa or lambda type.

The immunoglobulins of the present invention can be monovalent, divalent or polyvalent. Monovalent immunoglobulins are dimers (HL) formed of a chimeric heavy chain associated through disulfide bridges with a chimeric light chain. Divalent immunoglobulins are tetramers ($H_2L_2$) formed of two dimers associated through at least one disulfide bridge.

Standard Recombinant DNA Techniques

Standard recombinant DNA techniques are described in Sambrook et al., "Molecular Cloning," Second Edition, Cold Spring Harbor Laboratory Press (1987) and by Ausubel et al.(Eds) "Current Protocols in Molecular Biology," Green Publishing Associates/Wiley-Interscience, New York (1990).

Briefly, a suitable source of cells containing nucleic acid molecules that express the desired DNA, such as an antibody or antibody equivalent, is selected. Total RNA is prepared by standard procedures from a suitable source. The total RNA is used to direct cDNA synthesis. Standard methods for isolating RNA and synthesizing cDNA are provided in standard manuals of molecular biology such as, for example, those described above.

The cDNA may be amplified by known methods. For example, the cDNA may be used as a template for amplification by polymerase chain reaction (PCR); see Saiki et al., *Science,* 239, 487, 1998 or Mullis et al., U.S. Pat. No. *83,195. The sequences of the old* nucleotide primers for the PCR amplification are derived from the known sequence to be amplified. The oligonucleotides are synthesized by methods known in the art. Suitable methods include those described by Caruthers in *Science* 230, 281–285, 1985.

A mixture of upstream and downstream oligonucleotides are used in the PCR amplification. The conditions are optimized for each particular primer pair of according to standard procedures. The PCR product is analyzed, for example, by electrophoresis for cDNA having the correct size, corresponding to the sequence between the primers.

Alternatively, the coding region may be amplified in two or more overlapping fragments. The overlapping fragments are designed to include a restriction site permitting the assembly of the intact cDNA from the fragments.

In order to isolate the entire protein-coding regions for the heavy and light chains of each monoclonal antibody from each heterohybridoma cell line, for example, the upstream PCR oligonucleotide primer is complementary to the sequence at the 5' end, encompassing the ATG start codon and at least 5–10 nucleotides upstream of the start codon. The downstream PCR oligonucleotide primer is complementary to the sequence at the 3' end of the desired DNA sequence. The desired cDNA encodes the entire portion of the heavy and light chains of each monoclonal antibody, including the stop codon.

The cDNA to be amplified, such as the encoding the antibodies or antibody equivalents, may also be replicated in a wide variety of cloning vectors in a wide variety of host cells. The host cell may be prokaryotic or eukaryotic.

The vector into which the monoclonal antibody cDNA is spliced may comprise segments of chromosomal, non-chromosomal and synthetic DNA sequences. Some suitable prokaryotic cloning vectors include, but are not limited to, plasmids from *E. coli,* such as colE1, pCR1, pBR322, pMB9, pUC, pKSM, and RP4. Prokaryotic vectors also include, but are not limited to, derivatives of phage DNA such as M13 and other filamentous single-stranded DNA phages.

The vector containing the monoclonal antibody cDNA to be expressed is transfected into a suitable host cell, as described infra. The host cell is maintained in an appropriate culture medium, and subjected to conditions under which the cells and the vector replicate.

Chimeric Antibodies

In general, the chimeric antibodies are produced by preparing, for each of the light and heavy chain components of the chimeric immunoglobulin, a fused gene comprising a first DNA segment that encodes at least the functional portion of the human rabies virus specific neutralizing, preferably glycoprotein, human variable region linked (e.g., functionally rearranged variable region with joining segment) to a second DNA segment encoding at least a part of human constant region. Each fused gene is assembled in or inserted into an expression vector. Recipient cells capable of expressing the gene products are then transfected with the genes. The transfected recipient cells are cultured under conditions that permit expression of the incorporated genes and the expressed immunoglobulins or immunoglobulin chains are recovered.

Genes encoding the variable region of immunoglobulin heavy and light chains are obtained from lymphoid cells that produce the monoclonal rabies virus neutralizing antibodies. For example, the heterohybridoma cell lines that produce monoclonal antibody against the rabies glycoprotein provide a source of immunoglobulin variable region for the present chimeric antibodies. Constant regions are obtained from human antibody-producing cells by standard cloning techniques. Alternatively, because genes are representing the two classes of light chains an the give classes of heavy chains have been cloned, constant regions of human origin are readily available from these clones. Chimeric antibody binding fragments such as F(ab').sub.2 and Fab fragments are prepared by designing a chimeric heavy chain gene in truncated form. For example, a chimeric gene encoding a F(ab').sub.2 heavy chain portion would include DNA sequences encoding the CH, domain and hinge region of the heavy chain. Alternatively, such fragments can be obtained by enzymatic cleavage of a chimeric immunoglobulin. For instance, papain or pepsin cleavage can generate Fab or F(ab').sub.2 fragments, respectively.

Preferably, the fused genes encoding the heavy and light chimeric chains, or portions thereof, are assembled into two different expression vectors that can be used to cotransfect a recipient cell. Each vector contains two selectable genes, one for selection in a bacterial system, and one for selection in a eukaryotic system, each vector having a different pair of genes. These vectors allow production and amplification of the fused genes in bacterial system, and subsequent cotransfection of eukaryotic cells and selection of the cotransfected cells. Examples of selectable genes for the bacterial system include, but are not limited to, the genes that confer ampicillin resistance and the gene that confers chloramphenicol resistance. Two selectable genes for selection of eukaryotic transfectants are preferred, but are not limited to: (i) the xanthine-guanine phosphoribosyltransferase gene (gpt), and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid, which blocks the conversion of inosine monophosphate to xanthine monosphosphate, only cells expressing the gpt gene can survive. The product of the neo blocks the inhibition of protein synthesis in eukaryotic cells caused by the antibiotic G418 and other antibiotics of its class. The two selection procedures can be used simultaneously or sequentially to select for the expression of immunoglobulin chain genes introduced on two different DNA vectors into a eukaryotic cell.

Expression Systems

Due to the inherent degeneracy of the genetic code, other DNA sequences which encode substantially the same or a functionally equivalent heavy and light chain amino acid sequences, is within the scope of the invention. Altered DNA sequences which may be used in accordance with the invention include deletions, additions or substitutions of different nucleotide residues resulting in a sequence that encodes the same, or a functionally equivalent, gene product. The gene product itself may contain deletions, additions or substitutions of amino acid residues within a heavy or light chain sequence which result in a silent change, thus producing a functionally equivalent monoclonal antibody.

In accordance with the present invention, nucleotide sequences coding for heavy and light chains of the monoclonal rabies virus neutralizing antibody, a fragment or analog thereof, are inserted into an appropriate expression vector. This vector which contains the necessary elements for transcription and translation of the inserted protein-coding sequence so as to generate recombinant DNA molecules that direct the expression of heavy and light chain immunoglobulins for the formation of monoclonal rabies virus neutralizing antibody.

The preferred recipient cell line is a myeloma cell. Mycloma cells can synthesize, assemble and secrete immunoglobulins encoded by transfected immunoglobulin genes. Further, they possess the mechanism for glycosylation of the immunoglobulin. A particularly preferred recipient cell is a myeloma cell line that does not produce immunoglobulin, such as Sp2/0. These cell lines produce only the immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Several methods exist for transfecting lymphoid cells with vectors containing immunoglobulin encoding genes. A preferred way of introducing DNA into lymphoid cells is by electroporation. In this procedure recipient cells are subjected to an electric pulse in the presence of the DNA to be incorporated. Another way to introduce DNA is by protoplast fusion. In this method, lysozyme is used to strip cell walls from bacteria harboring the recombinant plasmid containing the immunoglobulin gene. The resulting spheroplasts are fused with myeloma cells with polyethylene glycol. After protoplast fusion, the transfectants are selected and isolated. Another technique that can be used to introduce DNA into may cell types is calcium phosphate precipitation.

The immunoglobulin genes can also be expressed in nonlymphoid cells, such as bacteria or yeast. When expressed in bacteria, the immunoglobulin heavy chains and light chains become part of inclusion bodies. Thus, the chains must be isolated and purified and then assembled into functional immunoglobulin molecules. Other strategies for expression in *E. coli* are available (see e.g., Pluckthun, A., *BioTechnology* 9:545–551, 1991; Skerra, A. et al., *BioTechnology* 9:273–278, 1991), including secretion from *E.coli* as fusion proteins comprising a signal sequence.

Example 2

The entire sequence of two monoclonal antibodies against the rabies virus, MAb 57 and MAb JB.1 were determined. The monoclonal antibodies bind specifically to the glycoprotein of various rabies virus strains. Post-exposure treatment, as well as prophylactic treatment, with a cocktail of monoclonal antibodies neutralizes the rabies virus at the site of entry and prevents the virus from spreading to the central nervous system (CNS). Thus, for transdermal or mucosal exposure to rabies virus, a cocktail of rabies specific-monoclonal antibodies are instilled into the bite site, as well as administered systemically. Since viral replication is restricted almost exclusively to neuronal cells, neutralization and clearance of the virus by the monoclonal antibodies of the present invention prior to entry into the CNS is an effective post-exposure prophylaxis.

A cocktail of monoclonal antibodies against rabies virus is delivered to the patient that has been exposed, or is at high risk of exposure, to rabies virus. The cocktail of monoclonal antibodies of the present invention effectively inhibits the formation of any rabies variants that can escape neutralization, as each monoclonal antibody in the cocktail of monoclonal antibodies has specificity for an epitope that is conserved in different street rabies viruses.

The nucleotide sequence of human anti-rabies MAb JB.1 heavy chain is SEQ ID NO:9.

The amino acid sequence of human anti-rabies MAb JB.1 heavy chain is SEQ ID NO:10.

The nucleotide sequence of human anti-rabies MAb JB.1 light chain is SEQ ID NO:11.

The amino acid sequence of human anti-rabies MAb JB.1 light chain is SEQ ID NO:12.

The nucleotide sequence of human anti-rabies MAb 57 light chain is SEQ ID NO:13.

The amino acid sequence of human anti-rabies MAb 57 light chain is SEQ ID NO:14.

The nucleotide sequence of human anti-rabies MAb 57 heavy chain is SEQ ID NO:15.

The amino acid sequence of human anti-rabies MAb 57 heavy chain is SEQ ID NO:16.

What is claimed is:

1. An isolated nucleic acid molecule encoding a polypeptide having the amino acid sequence SEQ ID NO:10.
2. An isolated nucleic acid molecule of claim 1 comprising the nucleotide sequence SEQ ID NO:9.
3. A recombinant expression vector comprising a nucleic acid molecule of claim 1.
4. A host cell comprising an expression vector of claim 3.
5. A recombinant expression vector comprising a nucleic acid molecule of claim 2.
6. A host cell comprising an expression vector of claim 5.
7. An isolated nucleic acid molecule encoding a polypeptide having the amino acid sequence SEQ ID NO:12.
8. An isolated nucleic acid molecule of claim 7 comprising the nucleotide sequence SEQ ID NO:11.
9. A recombinant expression vector comprising a nucleic acid molecule of claim 7.
10. A recombinant expression vector comprising a nucleic acid molecule of claim 8.

11. A host cell comprising an expression vector of claim 9.

12. A host cell comprising an expression vector of claim 10.

13. A recombinant expression vector comprising the nucleic acid molecule of claim 2 and the nucleic acid molecule of claim 7.

14. A recombinant expression vector comprising the nucleic acid molecule of claim 3 and the nucleic acid molecule of claim 8.

15. A host cell comprising the expression vector of claim 13.

16. A host cell comprising the expression vector of claim 14.

* * * * *

SEQUENCE LISTING

<160> NUMBER OF SEQ ID NOS: 16

<210> SEQ ID NO 1
<211> LENGTH: 1430
<212> TYPE: DNA
<213> ORGANISM: Homo sapiens

<400> SEQUENCE: 1

| | | | | | |
|---|---|---|---|---|---|
| accatggagt | ttgggctgag | ctggcttttt | cttgtggcta | ttttaaaagg | tgtccagtgt | 60 |
| gaggtgcagc | tgttggagtc | tgggggaggc | ttggtacagc | ctggggggtc | cctgagactc | 120 |
| tcctgtgcag | cctctggatt | cacctttagc | aactatgcca | tgagctgggt | ccgccaggct | 180 |
| ccagggaagg | ggctggagtg | gtctcagct | attagtgcta | gtggtcatag | cacatatttg | 240 |
| gcagactccg | tgaagggccg | gttcaccatc | tccagagaca | attccaagaa | cacgctgtat | 300 |
| ctgcaaatga | acagcctgag | agccgaggac | acggccgtat | attactgtgc | gaaagatcga | 360 |
| gaggttacta | tgatagttgt | acttaatgga | ggctttgact | actggggcca | gggaacccgg | 420 |
| gtcaccgtct | cctccgcctc | caccaagggc | ccatcggtct | tccccctggc | accctcctcc | 480 |
| aagagcacct | ctgggggcac | agcggccctg | ggctgcctgg | tcaaggacta | cttccccgaa | 540 |
| ccggtgacgg | tgtcgtggaa | ctcaggcgcc | ctgaccagcg | gcgtgcacac | cttcccggct | 600 |
| gtcctacagt | cctcaggact | ctactccctc | agcagcgtgg | tgaccgtgcc | ctccagcagc | 660 |
| ttgggcaccc | agacctacat | ctgcaacgtg | aatcacaagc | ccagcaacac | caaggtggac | 720 |
| aagagagttg | agcccaaatc | ttgtgacaaa | actcacacat | gcccaccgtg | cccagcacct | 780 |
| gaactcctgg | ggggaccgtc | agtcttcctc | ttccccccaa | aacccaagga | caccctcatg | 840 |
| atctcccgga | cccctgaggt | cacatgcgtg | gtggtggacg | tgagccacga | agaccctgag | 900 |
| gtcaagttca | actggtacgt | ggacggcgtg | gaggtgcata | atgccaagac | aaagccgcgg | 960 |
| gaggagcagt | acaacagcac | gtaccgtgtg | gtcagcgtcc | tcaccgtcct | gcaccaggac | 1020 |
| tggctgaatg | gcaaggagta | caagtgcaag | gtctccaaca | aagccctccc | agcccccatc | 1080 |
| gagaaaacca | tctccaaagc | caaagggcag | ccccgagaac | cacaggtgta | caccctgccc | 1140 |
| ccatcccggg | aggagatgac | caagaaccag | gtcagcctga | cctgcctggt | caaaggcttc | 1200 |
| tatcccagcg | acatcgccgt | ggagtgggag | agcaatgggc | agccggagaa | caactacaag | 1260 |
| accacgcctc | ccgtgctgga | ctccgacggc | tccttcttcc | tctatagcaa | gctcaccgtg | 1320 |
| gacaagagca | ggtggcagca | ggggaacgtc | ttctcatgct | ccgtgatgca | tgaggctctg | 1380 |
| cacaaccact | acacgcagaa | gagcctctcc | ctgtccccgg | gtaaatgagt | | 1430 |

<210> SEQ ID NO 2
<211> LENGTH: 708
<212> TYPE: DNA
<213> ORGANISM: Homo sapiens

<400> SEQUENCE: 2

| | | | | | |
|---|---|---|---|---|---|
| agcatggaag | ccccagctca | gcttctcttc | ctcctgctac | tctggctccc | agataccacc | 60 |
| ggagaaattg | tgttgacaca | gtctccagcc | accctgtctt | tgtctccagg | ggaaagagcc | 120 |
| accctcgcct | gcagggccag | tcagactgct | agcaggtact | tagcctggta | ccaacagaaa | 180 |
| cctggccagg | ctcccagact | cctcatctat | gatacatcca | acagggccac | tggcatccca | 240 |
| gccaggttca | gtgcagtggg | gtctgggaca | gacttcactc | tctccatcag | cagcctggag | 300 |
| cctgaagatt | ttgcagtttta | ttactgtcag | cagcgtttca | ctggccgtg | gacgttcggc | 360 |

-continued

```
caagggacca aggtggaatt caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag     660
ggcctgagct cgcccgtcac aaagagcttc aacaggggag agtgttag                 708
```

```
<210> SEQ ID NO 3
<211> LENGTH: 474
<212> TYPE: PRT
<213> ORGANISM: Homo sapiens

<400> SEQUENCE: 3
```

| | | | | | | | | | | | | | | | |
|---|---|---|---|---|---|---|---|---|---|---|---|---|---|---|---|
| Met | Glu | Phe | Gly | Leu | Ser | Trp | Leu | Phe | Leu | Val | Ala | Ile | Leu | Lys | Gly |
| 1 | | | | 5 | | | | | 10 | | | | | 15 | |
| Val | Gln | Cys | Glu | Val | Gln | Leu | Leu | Glu | Ser | Gly | Gly | Gly | Leu | Val | Gln |
| | | | 20 | | | | | 25 | | | | | 30 | | |
| Pro | Gly | Gly | Ser | Leu | Arg | Leu | Ser | Cys | Ala | Ala | Ser | Gly | Phe | Thr | Phe |
| | | 35 | | | | | 40 | | | | | 45 | | | |
| Ser | Asn | Tyr | Ala | Met | Ser | Trp | Val | Arg | Gln | Ala | Pro | Gly | Lys | Gly | Leu |
| | 50 | | | | | 55 | | | | | 60 | | | | |
| Glu | Trp | Val | Ser | Ala | Ile | Ser | Ala | Ser | Gly | His | Ser | Thr | Tyr | Leu | Ala |
| 65 | | | | | 70 | | | | | 75 | | | | | 80 |
| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | |
| Thr | Leu | Tyr | Leu | Gln | Met | Asn | Ser | Leu | Arg | Ala | Glu | Asp | Thr | Ala | Val |
| | | | 100 | | | | | 105 | | | | | 110 | | |
| Tyr | Tyr | Cys | Ala | Lys | Asp | Arg | Glu | Val | Thr | Met | Ile | Val | Val | Leu | Asn |
| | | 115 | | | | | 120 | | | | | 125 | | | |
| Gly | Gly | Phe | Asp | Tyr | Trp | Gly | Gln | Gly | Thr | Arg | Val | Thr | Val | Ser | Ser |
| | 130 | | | | | 135 | | | | | 140 | | | | |
| Ala | Ser | Thr | Lys | Gly | Pro | Ser | Val | Phe | Pro | Leu | Ala | Pro | Ser | Ser | Lys |
| 145 | | | | | 150 | | | | | 155 | | | | | 160 |
| Ser | Thr | Ser | Gly | Gly | Thr | Ala | Ala | Leu | Gly | Cys | Leu | Val | Lys | Asp | Tyr |
| | | | | 165 | | | | | 170 | | | | | 175 | |
| Phe | Pro | Glu | Pro | Val | Thr | Val | Ser | Trp | Asn | Ser | Gly | Ala | Leu | Thr | Ser |
| | | | 180 | | | | | 185 | | | | | 190 | | |
| Gly | Val | His | Thr | Phe | Pro | Ala | Val | Leu | Gln | Ser | Ser | Gly | Leu | Tyr | Ser |
| | | 195 | | | | | 200 | | | | | 205 | | | |
| Leu | Ser | Ser | Val | Val | Thr | Val | Pro | Ser | Ser | Ser | Leu | Gly | Thr | Gln | Thr |
| | 210 | | | | | 215 | | | | | 220 | | | | |
| Tyr | Ile | Cys | Asn | Val | Asn | His | Lys | Pro | Ser | Asn | Thr | Lys | Val | Asp | Lys |
| 225 | | | | | 230 | | | | | 235 | | | | | 240 |
| Arg | Val | Glu | Pro | Lys | Ser | Cys | Asp | Lys | Thr | His | Thr | Cys | Pro | Pro | Cys |
| | | | | 245 | | | | | 250 | | | | | 255 | |
| Pro | Ala | Pro | Glu | Leu | Leu | Gly | Gly | Pro | Ser | Val | Phe | Leu | Phe | Pro | Pro |
| | | | 260 | | | | | 265 | | | | | 270 | | |
| Lys | Pro | Lys | Asp | Thr | Leu | Met | Ile | Ser | Arg | Thr | Pro | Glu | Val | Thr | Cys |
| | | 275 | | | | | 280 | | | | | 285 | | | |
| Val | Val | Val | Asp | Val | Ser | His | Glu | Asp | Pro | Glu | Val | Lys | Phe | Asn | Trp |
| | 290 | | | | | 295 | | | | | 300 | | | | |
| Tyr | Val | Asp | Gly | Val | Glu | Val | His | Asn | Ala | Lys | Thr | Lys | Pro | Arg | Glu |

```
                305                 310                 315                 320

Glu Gln Tyr Asn Ser Thr Tyr Arg Val Val Ser Val Leu Thr Val Leu
                    325                 330                 335

His Gln Asp Trp Leu Asn Gly Lys Glu Tyr Lys Cys Lys Val Ser Asn
                    340                 345                 350

Lys Ala Leu Pro Ala Pro Ile Glu Lys Thr Ile Ser Lys Ala Lys Gly
                    355                 360                 365

Gln Pro Arg Glu Pro Gln Val Tyr Thr Leu Pro Pro Ser Arg Glu Glu
                    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                    405                 410                 415

Asn Tyr Lys Thr Thr Pro Pro Val Leu Asp Ser Asp Gly Ser Phe Phe
                    420                 425                 430

Leu Tyr Ser Lys Leu Thr Val Asp Lys Ser Arg Trp Gln Gln Gly Asn
                    435                 440                 445

Val Phe Ser Cys Ser Val Met His Glu Ala Leu His Asn His Tyr Thr
                    450                 455                 460

Gln Lys Ser Leu Ser Leu Ser Pro Gly Lys
465                 470

<210> SEQ ID NO 4
<211> LENGTH: 234
<212> TYPE: PRT
<213> ORGANISM: Homo sapiens

<400> SEQUENCE: 4

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ala Cys Arg Ala Ser Gln Thr
            35                  40                  45

Ala Ser Arg Tyr Leu Ala Trp Tyr Gln Gln Lys Pro Gly Gln Ala Pro
    50                  55                  60

Arg Leu Leu Ile Tyr Asp Thr Ser Asn Arg Ala Thr Gly Ile Pro Ala
65                  70                  75                  80

Arg Phe Ser Gly Ser Gly Ser Gly Thr Asp Phe Thr Leu Ser Ile Ser
                85                  90                  95

Ser Leu Glu Pro Glu Asp Phe Ala Val Tyr Tyr Cys Gln Gln Arg Phe
                100                 105                 110

Asn Trp Pro Trp Thr Phe Gly Gln Gly Thr Lys Val Glu Phe Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205
```

```
His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 5
<211> LENGTH: 20
<212> TYPE: DNA
<213> ORGANISM: Homo sapiens

<400> SEQUENCE: 5
accatggagt ttgggctgag                                            20

<210> SEQ ID NO 6
<211> LENGTH: 20
<212> TYPE: DNA
<213> ORGANISM: Homo sapiens

<400> SEQUENCE: 6
actcatttac ccggggacag                                            20

<210> SEQ ID NO 7
<211> LENGTH: 20
<212> TYPE: DNA
<213> ORGANISM: Homo sapiens

<400> SEQUENCE: 7
agcatggaag ccccagctca                                            20

<210> SEQ ID NO 8
<211> LENGTH: 21
<212> TYPE: DNA
<213> ORGANISM: Homo sapiens

<400> SEQUENCE: 8
ctctaacact ctcccctgtt g                                          21

<210> SEQ ID NO 9
<211> LENGTH: 1557
<212> TYPE: DNA
<213> ORGANISM: Homo sapiens

<400> SEQUENCE: 9
atggacacac tttgctccac gctcctgctg ctgaccatcc cttcatgggt cttgtcccaa     60
attaccttga aggagactgg tcctacgctg gtgaaaccca cacagaccct cacgctgacc    120
tgcaccttct cggggttctc actcagcact agtggagtgg gtgtgggctg gatccgtcag    180
cccccaggaa aggccctgga gtgggttaca ctcatttatt gggatgatga taagcgttac    240
agtccatctc tggagaacag ggtcaccatc aggaaggaca cctccaaaaa ccaggtggct    300
cttacaatga cgaacatgga ccctttggac acaggcacat actactgtgc gcacagacaa    360
catatcagca gcttcccgtg gttcgattcc tggggccagg gaaccctggt caccgtctcc    420
tcagcttcca ccaagggccc atcggtcttc cccctggcgc cctgctccag gagcacctct    480
gggggcacag cggccctggg ctgcctggtc aaggactact cccccgagcc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacacct gcaacgtgaa tcacaagccc agcaacacca aggtggacaa gagagttgag    720
ctcaaaaccc cacttggtga cacaactcac acatgcccac ggtgcccaga gcccaaatct    780

```
tgtgacacac ctcccccgtg cccacggtgc ccagagccca atcttgtga cacacctccc    840 ccgtgcccac ggtgcccaga gcccaaatct tgtgacacac ctcccccatg cccacggtgc    900
ccagcacctg aactcctggg aggaccgtca gtcttcctct ccccccaaa acccaaggat    960 acccttatga tttcccggac ccctgaggtc acgtgcgtgg tggtggacgt gagccacgaa   1020
gaccccgagg tccagttcaa gtggtacgtg gacggcgtgg aggtgcataa tgccaagaca   1080
aagccgcggg aggagcagtt caacagcacg ttccgtgtgg tcagcgtcct caccgtcctg   1140
caccaggact ggctgaacgg taaggagtac aagtgcaagg tctccaacaa agccctccca   1200
gcccccatcg agaaaaccat ctccaaaacc aaggacagc cccgagaacc acaggtgtac    1260
accctgcccc catcccggga ggagatgacc aagaaccagg tcagcctgac ctgcctggtc   1320
aaaggcttct accccagcga catcgccgtg gagtgggaga gcagcgggca gccggagaac   1380
aactacaaca ccacgcctcc catgctggac tccgacggct ccttcttcct ctacagcaag   1440
ctcaccgtgg acaagagcag gtggcagcag gggaacatct tctcatgctc cgtgatgcat   1500
gaggctctgc acaaccgctt cacgcagaag agcctctccc tgtctccggg taaatga      1557
```

<210> SEQ ID NO 10
<211> LENGTH: 518
<212> TYPE: PRT
<213> ORGANISM: Homo sapiens

<400> SEQUENCE: 10

```
Met Asp Thr Leu Cys Ser Thr Leu Leu Leu Thr Ile Pro Ser Trp
  1               5                  10                  15

Val Leu Ser Gln Ile Thr Leu Lys Glu Thr Gly Pro Thr Leu Val Lys
                 20                  25                  30

Pro Thr Gln Thr Leu Thr Leu Thr Cys Thr Phe Ser Gly Phe Ser Leu
             35                  40                  45

Ser Thr Ser Gly Val Gly Val Gly Trp Ile Arg Gln Pro Pro Gly Lys
         50                  55                  60

Ala Leu Glu Trp Val Thr Leu Ile Tyr Trp Asp Asp Asp Lys Arg Tyr
 65                  70                  75                  80

Ser Pro Ser Leu Glu Asn Arg Val Thr Ile Arg Lys Asp Thr Ser Lys
                 85                  90                  95

Asn Gln Val Ala Leu Thr Met Thr Asn Met Asp Pro Leu Asp Thr Gly
            100                 105                 110

Thr Tyr Tyr Cys Ala His Arg Gln His Ile Ser Phe Pro Trp Phe
            115                 120                 125

Asp Ser Trp Gly Gln Gly Thr Leu Val Thr Val Ser Ser Ala Ser Thr
        130                 135                 140

Lys Gly Pro Ser Val Phe Pro Leu Ala Pro Cys Ser Arg Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Thr Cys
    210                 215                 220

Asn Val Asn His Lys Pro Ser Asn Thr Lys Val Asp Lys Arg Val Glu
225                 230                 235                 240
```

```
Leu Lys Thr Pro Leu Gly Asp Thr Thr His Thr Cys Pro Arg Cys Pro
                245                 250                 255

Glu Pro Lys Ser Cys Asp Thr Pro Pro Cys Pro Arg Cys Pro Glu
            260                 265                 270

Pro Lys Ser Cys Asp Thr Pro Pro Cys Pro Arg Cys Pro Glu Pro
        275                 280                 285

Lys Ser Cys Asp Thr Pro Pro Cys Pro Arg Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Gln Phe Lys Trp Tyr Val Asp Gly
            340                 345                 350

Val Glu Val His Asn Ala Lys Thr Lys Pro Arg Glu Glu Gln Phe Asn
        355                 360                 365

Ser Thr Phe Arg Val Val Ser Val Leu Thr Val Leu His Gln Asp Trp
    370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Thr Lys Gly Gln Pro Arg Glu
                405                 410                 415

Pro Gln Val Tyr Thr Leu Pro Pro Ser Arg Glu Glu Met Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Ser Gly Gln Pro Glu Asn Asn Tyr Asn Thr
    450                 455                 460

Thr Pro Pro Met Leu Asp Ser Asp Gly Ser Phe Phe Leu Tyr Ser Lys
465                 470                 475                 480

Leu Thr Val Asp Lys Ser Arg Trp Gln Gln Gly Asn Ile Phe Ser Cys
                485                 490                 495

Ser Val Met His Glu Ala Leu His Asn Arg Phe Thr Gln Lys Ser Leu
            500                 505                 510

Ser Leu Ser Pro Gly Lys
        515

<210> SEQ ID NO 11
<211> LENGTH: 699
<212> TYPE: DNA
<213> ORGANISM: Homo sapiens

<400> SEQUENCE: 11
atggcctgga ccgttctcct cctcggcctc ctctctcact gcacagggtc tgtgacgtcc    60
tatgtgctga ctcagccacc ctcggtgtca gtggccccag gaaagacggc caggattaac   120
tgtgggggaa acaacattga atatagaagt gtgcactggt accagcagaa gtcaggccag   180
gcccctgtag cggtcatcta tgataatagt gaccggccct cagggatccc tgagcgattc   240
tctggttcca atctgggaa cacgccacc ctgaccatca gcagggtcga agccggggat   300
gaggccgact attactgtca ggtgtgggat attagtagtg atgtggtctt cggcggaggg   360
accaagctga ccgtcctagg tcagcccaag gctgccccct cggtcactct gttcccgccc   420
tcctctgagg agcttcaagc caacaaggcc acactggtgt gtctcataag tgacttctac   480
```

```
ccgggagccg tgacagtggc ctggaaggca gatagcagcc ccgtcaaggc gggagtggag    540
accaccacac cctccaaaca agcaacaac  aagtacgcgg ccagcagcta tctgagcctg    600
acgcctgagc agtggaagtc ccacagaagc tacagctgcc aggtcacgca tgaagggagc    660
accgtggaga agacagtggc ccctacagaa tgttcatag                            699
```

<210> SEQ ID NO 12
<211> LENGTH: 232
<212> TYPE: PRT
<213> ORGANISM: Homo sapiens

<400> SEQUENCE: 12

```
Met Ala Trp Thr Val Leu Leu Leu Gly Leu Leu Ser His Cys Thr Gly
 1               5                  10                  15

Ser Val Thr Ser Tyr Val Leu Thr Gln Pro Pro Ser Val Ser Val Ala
            20                  25                  30

Pro Gly Lys Thr Ala Arg Ile Asn Cys Gly Gly Asn Asn Ile Glu Tyr
        35                  40                  45

Arg Ser Val His Trp Tyr Gln Gln Lys Ser Gly Gln Ala Pro Val Ala
    50                  55                  60

Val Ile Tyr Asp Asn Ser Asp Arg Pro Ser Gly Ile Pro Glu Arg Phe
65                  70                  75                  80

Ser Gly Ser Lys Ser Gly Asn Thr Ala Thr Leu Thr Ile Ser Arg Val
                85                  90                  95

Glu Ala Gly Asp Glu Ala Asp Tyr Tyr Cys Gln Val Trp Asp Ile Ser
           100                 105                 110

Ser Asp Val Val Phe Gly Gly Gly Thr Lys Leu Thr Val Leu Gly Gln
       115                 120                 125

Pro Lys Ala Ala Pro Ser Val Thr Leu Phe Pro Pro Ser Ser Glu Glu
   130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
           180                 185                 190

Ala Ala Ser Ser Tyr Leu Ser Leu Thr Pro Glu Gln Trp Lys Ser His
       195                 200                 205

Arg Ser Tyr Ser Cys Gln Val Thr His Glu Gly Ser Thr Val Glu Lys
   210                 215                 220

Thr Val Ala Pro Thr Glu Cys Ser
225                 230
```

<210> SEQ ID NO 13
<211> LENGTH: 726
<212> TYPE: DNA
<213> ORGANISM: Homo sapiens

<400> SEQUENCE: 13

```
atgagtgtcc ccaccatggc ctgggctctg ctcctcctca gcctcctcac tcagggcaca    60
ggatcctggg ctcagtctgc cctgactcag cctcgctcag tgtccgggtc tcctggacag   120
tcagtcacca tctcctgcac tggaaccagc agtgatattg gtggttataa ctttgtctcc   180
tggtaccaac aacacccagg caaagccccc aaactcatga tttatgatgc cactaagcgg   240
ccctcagggg tccctgatcg cttctctggc tccaagtctg gcaacacggc ctccctgacc   300
```

-continued

```
atctctgggc tccaggctga ggatgaggct gattattact gctgctcata tgcaggcgac    360
tacaccccgg gcgtggtttt cggcggaggg accaagctga ccgtcctagg tcagcccaag    420
gctgccccct cggtcactct gttcccgccc tcctctgagg agcttcaagc caacaaggcc    480
acactggtgt gtctcataag tgacttctac ccgggagccg tgacagtggc ctggaaggca    540
atagcagccc cgtcaaggcg ggagtggaga ccaccacacc ctccaaacaa agcaacaaca    600
gtacgcggcc agcagctacc tgagcctgac gcctgagcag tggaagtccc acagaagcac    660
agctgccagg tcacgcatga agggagcacc gtggagaaga cagtggcccc tacagaatgt    720
tcatag                                                               726
```

<210> SEQ ID NO 14
<211> LENGTH: 242
<212> TYPE: PRT
<213> ORGANISM: Homo sapiens

<400> SEQUENCE: 14

```
Met Ser Val Pro Thr Met Ala Trp Ala Leu Leu Leu Ser Leu Leu
  1               5                  10                  15

Thr Gln Gly Thr Gly Ser Trp Ala Gln Ser Ala Leu Thr Gln Pro Arg
             20                  25                  30

Ser Val Ser Gly Ser Pro Gly Gln Ser Val Thr Ile Ser Cys Thr Gly
         35                  40                  45

Thr Ser Ser Asp Ile Gly Gly Tyr Asn Phe Val Ser Trp Tyr Gln Gln
     50                  55                  60

His Pro Gly Lys Ala Pro Lys Leu Met Ile Tyr Asp Ala Thr Lys Arg
 65                  70                  75                  80

Pro Ser Gly Val Pro Asp Arg Phe Ser Gly Ser Lys Ser Gly Asn Thr
                 85                  90                  95

Ala Ser Leu Thr Ile Ser Gly Leu Gln Ala Glu Asp Glu Ala Asp Tyr
            100                 105                 110

Tyr Cys Cys Ser Tyr Ala Gly Asp Tyr Thr Pro Gly Val Val Phe Gly
        115                 120                 125

Gly Gly Thr Lys Leu Thr Val Leu Gly Gln Pro Lys Ala Ala Pro Ser
    130                 135                 140

Val Thr Leu Phe Pro Pro Ser Ser Glu Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Lys Ser His Arg Ser Tyr Ser Cys Gln
    210                 215                 220

Val Thr His Glu Gly Ser Thr Val Glu Lys Thr Val Ala Pro Thr Glu
225                 230                 235                 240

Cys Ser
```

<210> SEQ ID NO 15
<211> LENGTH: 1431
<212> TYPE: DNA
<213> ORGANISM: Homo sapiens

<400> SEQUENCE: 15

-continued

```
atggactgga cctggaggtt cctctttgtg gtggcagcag ctacaggtgt ccagtcccag      60
gtgcagctgg tgcagtctgg ggctgaggtg aagaagcctg gtcctcggt gaaggtctcc     120
tgcaaggctt ctggaggcac cttcaacagg tatactgtca actgggtgcg acaggcccct    180
ggacaagggc ttgagtggat gggaggcatc atccctatct ttggtacagc aaactacgca    240
cagaggttcc aggcagact caccattacc gcggacgaat ccacgagcac agcctacatg     300
gagctgagca gcctgagatc tgatgacacg gccgtgtatt tctgtgcgag agaatctc     360
gataattcgg ggacttatta ttatttctca ggctggttcg accctggggg ccagggaacc    420
ctggtcaccg tctcctcagc ctccaccaag ggcccatcgg tcttcccct ggcaccctcc     480
tccaagagca cctctggggg cacagcggcc ctgggctgcc tggtcaagga ctacttcccc    540
gaaccggtga cggtgtcgtg gaactcaggc gccctgacca gcggcgtgca caccttcccg    600
gctgtcctac agtcctcagg actctactcc ctcagcagcg tggtgaccgt gccctccagc    660
agcttgggca cccagaccta catctgcaac gtgaatcaca agcccagcaa caccaaggtg    720
gacaagagag ttgagcccaa atcttgtgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggaggagat gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct cctctatag caagctcacc    1320
gtggacaaga gcaggtggca gcaggggaac gtcttctcat gctccgtgat gcatgaggct   1380
ctgcacaacc actacacgca gaagagcctc tccctgtccc cgggtaaatg a            1431
```

<210> SEQ ID NO 16
<211> LENGTH: 476
<212> TYPE: PRT
<213> ORGANISM: Homo sapiens

<400> SEQUENCE: 16

```
Met Asp Trp Thr Trp Arg Phe Leu Phe Val Val Ala Ala Ala Thr Gly
  1               5                  10                  15

Val Gln Ser Gln Val Gln Leu Val Gln Ser Gly Ala Glu Val Lys Lys
              20                  25                  30

Pro Gly Ser Ser Val Lys Val Ser Cys Lys Ala Ser Gly Gly Thr Phe
          35                  40                  45

Asn Arg Tyr Thr Val Asn Trp Val Arg Gln Ala Pro Gly Gln Gly Leu
      50                  55                  60

Glu Trp Met Gly Gly Ile Ile Pro Ile Phe Gly Thr Ala Asn Tyr Ala
 65                  70                  75                  80

Gln Arg Phe Gln Gly Arg Leu Thr Ile Thr Ala Asp Glu Ser Thr Ser
                  85                  90                  95

Thr Ala Tyr Met Glu Leu Ser Ser Leu Arg Ser Asp Asp Thr Ala Val
             100                 105                 110

Tyr Phe Cys Ala Arg Glu Asn Leu Asp Asn Ser Gly Thr Tyr Tyr Tyr
         115                 120                 125
```

```
Phe Ser Gly Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
                180                 185                 190

Thr Ser Gly Val His Thr Phe Pro Ala Val Leu Gln Ser Ser Gly Leu
            195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
    355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
    435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```